US00PP29406P2

(12) United States Plant Patent
Hansen

(10) Patent No.: US PP29,406 P2
(45) Date of Patent: Jun. 19, 2018

(54) ***VERONICA* PLANT NAMED 'BLUE SKYWALKER'**

(50) Latin Name: ***Veronica spicata* L.**
Varietal Denomination: Blue Skywalker

(71) Applicant: Hans A. Hansen, Zeeland, MI (US)

(72) Inventor: Hans A. Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 7 days.

(21) Appl. No.: 15/530,508

(22) Filed: Jan. 23, 2017

(51) Int. Cl.
*A01H 5/02* (2018.01)

(52) U.S. Cl.
USPC ..... Plt./251

(58) Field of Classification Search
USPC ..... Plt./251
See application file for complete search history.

*Primary Examiner* — Anne Marie Grunberg

(57) ABSTRACT

The new and distinct cultivar of ornamental spike speedwell plant, *Veronica* 'Blue Skywalker', with tight upright habit and stiff freely-branched branched spikes producing lavender blue flowers over a long period beginning early summer and if cut back hard may repeat in early fall.

1 Drawing Sheet

Botanical classification: *Veronica spicata* L.
Variety denomination: 'Blue Skywalker'.

BACKGROUND OF THE INVENTION

The present invention relates to the new and distinct cultivar of spike speedwell, botanically known as *Veronica spicata* 'Blue Skywalker', and hereinafter referred to as the cultivar 'Blue Skywalker' or the "new plant". The new plant was hybridized in the summer of 2012 by the inventor at a wholesale perennial nursery in Zeeland, Mich., USA, with 'White Wands' U.S. Plant Pat. No. 27,632 as the female parent and an unreleased proprietary hybrid known as K07-32-109 as the male parent. The cross was performed on Jun. 29, 2012 and the individual seedling that was ultimately named 'Blue Skywalker' was identified by the breeder code 12-37-01 throughout the trial period.

The new plant has been asexually propagated by shoot tip cuttings at the same nursery in the greenhouses in Zeeland, Mich., since the summer of 2014 with subsequent asexually propagated plants found to be identical to the original selection with all the same traits as the original. seedling.

No plants of *Veronica* 'Blue Skywalker' have been sold or disclosed by this or any other name, in this country or anywhere in the world, prior to one year from the filing of this application, with the exception of that was sold or disclosed within one year of the filing of this application and which was either derived directly or indirectly from the inventor.

BRIEF SUMMARY OF THE PLANT

*Veronica spicata* 'Blue Skywalker' is unique from all other spike speedwell known to the inventor. Several other cultivars may have some similar traits, but this is the only variety known by the inventor to have the following characteristic combinations that establish the new plant as unique:

1. Tight upright habit with stiff spikes above dense mats of foliage.

2. Scapes with numerous flowers of distinctly lavender blue petals.
3. Freely branched peduncles with long blooming season.

The closest comparison varieties to the new plant are 'Sunny Border Blue' (not patented), 'Goodness Grows' (not patented), 'Atomic Violet' U.S. Plant Pat. No. 21,780 and 'Atomic Blue' U.S. Plant Pat. No. 21,840. The new plant is more upright and has taller spikes than all of the above spike speedwell. The flower color of the new plant is more lavender blue than each of the above. Compared with the female parent the new plant has lavender blue flowers and not white as in 'White Wands' and the new plant is more upright and taller. Compared with the male parent the new plant has flowers that are more lavender-blue.

BRIEF DESCRIPTION OF THE DRAWINGS

The photograph of the new plant demonstrates the overall appearance and unique traits of 'Blue Skywalker' as a two-year-old plant grown in a full-sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
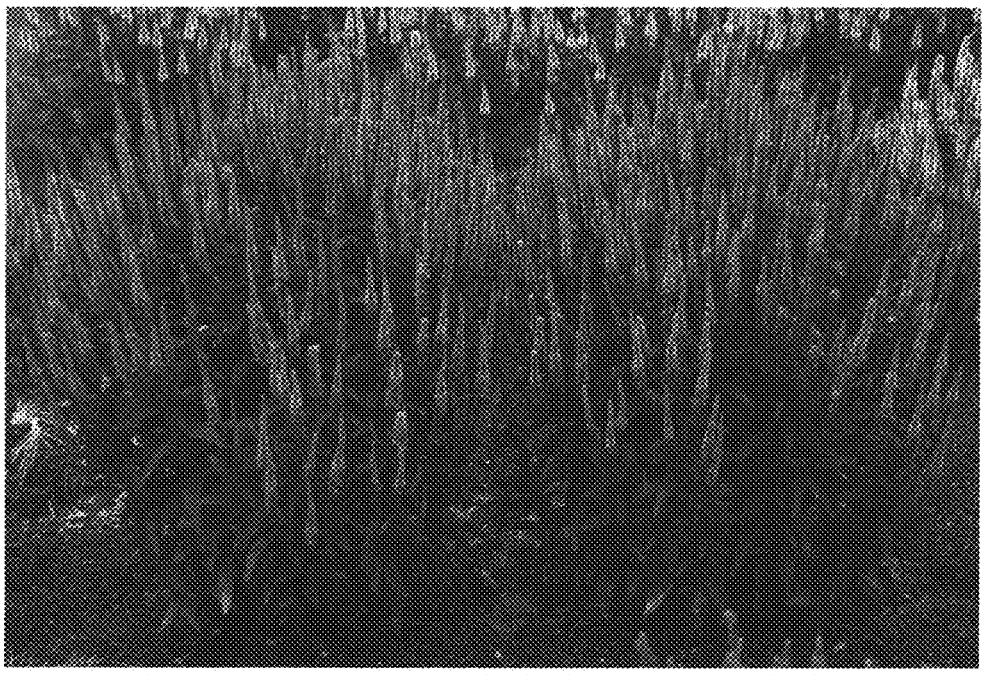
FIG. 1 shows the habit of two new plants in full flower.
Figure 2:
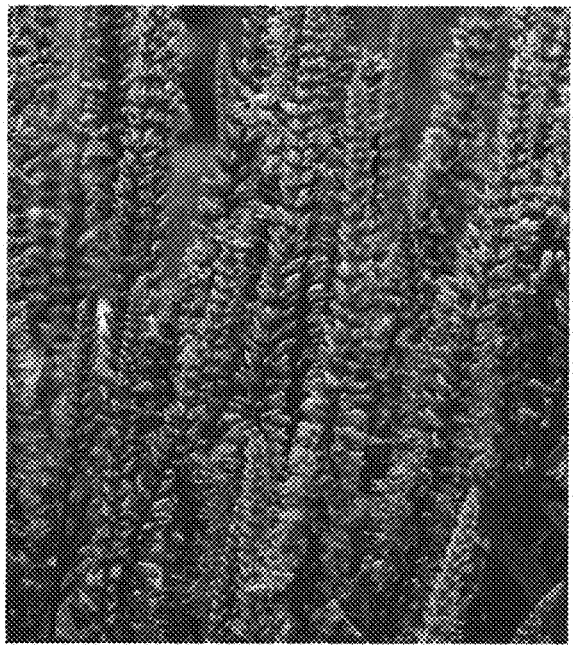
FIG. 2 shows a close-up of the flowers and buds.

The following descriptions and color references of *Veronica* 'Blue Skywalker' are based on the 2001 edition of The Royal Horticultural Society Colour Chart except where common dictionary terms are used. *Veronica* 'Blue Skywalker' has not been observed under all possible environments. The phenotype may vary slightly with different growing environments such as temperature, light, fertility, soil pH, moisture and maturity levels, but without any change in the genotype. The following observations and size descriptions are based on two-year old plants in the full sun trial garden of a nursery in Zeeland, Mich. with supplemental fertilizer and water as needed.

Botanical classification: *Veronica spicata;*

Parentage: Female (seed parent) *Veronica* 'White Wands'; male (pollen parent) breeder code K07-32-109;

Plant habit: Hardy herbaceous perennial, with average 40 branched stems, main stems blooming to about 70.0 cm tall and clumping to about 94 cm across; flowering beginning late June in Michigan and continuing for about 6 weeks with occasional repeat if deadheaded;

Leaves: Simple, flat, elliptic to lanceolate; opposite; serrated margin with about 3 teeth per one centimeter; glabrous below and above, acute apex, attenuate base; about 8.5 cm long by 1.8 cm wide decreasing in both length and width distally;

Leaf color: Mature leaves adaxial between RHS 137A than RHS 139A; abaxial nearest RHS 137C; young expanding leaves nearest RHS 144A above and below;

Veins: Reticulate, abaxial puberulent and glabrate to glabrous adaxial; abaxial midrib costate; about 1.0 mm across at abaxial base and about 0.5 mm at adaxial base;

Vein color: Adaxial midrib nearest RHS 147D and secondary veins between RHS 137A and RHS 139A; abaxial midrib nearest RHS 147D with secondary veins nearest RHS 137A;

Petiole: Simple, slightly concaved upward on edges, margin minutely ciliate; about 1.5 cm long and 4.0 mm wide length shorter and narrower on distal leaves;

Petiole color: Adaxial base nearest RHS 144D, distally between RHS 137A and RHS 139A; abaxial nearest RNS 144D;

Buds one to two days prior to opening: Convolute, narrowly oblong, obtuse apex; about 5.5 mm long and 2.5 mm diameter;

Bud color: Nearest RHS 90B throughout;

Flowers: On heavily branched upright spikes in compressed conglomerate; numerous; zygomorphic; campanulate; approximately 420 per main spike; about 8.0 mm long and about 7.0 mm across; flowers persist individually for 4 to 6 days whether on the plant or cut; petals self-cleaning, sepals and style persistent;

Flower timing: Early to mid-summer and repeating if deadheaded into early fall;

Flower fragrance: None detected;

Petals: Four; one larger petal above and three slightly smaller below and to either side; simple, entire, fused in basal 2.5 mm; glabrous abaxial and pubescent with 1.0 mm long hairs in tuft band about 1.0 to 2.0 mm from adaxial base; upper larger petal with rounded apex, about 5.5 mm long by 2.0 mm wide; side and lower petals with acute apex, about 5.5 mm long and 1.5 mm wide;

Petal color: Abaxial nearest RHS 90C and adaxial nearest RHS 90C with hairs inside tube white, whiter than RHS 155D;

Androecium:

*Filaments*.—Two; divergent; glabrous; epipetalous about 1.0 mm from base; about 5.5 mm long by about 0.25 mm diameter; color nearest RHS 83A.

*Anther*.—Dorsifixed, longitudinal; elliptic with acute apex and rounded base; about 1.5 mm by 1.0 mm; color nearest RHS 83C.

*Pollen*.—Abundant, globose, less than 0.1 mm; nearest RHS 8C.

Gynoecium: Single, superior; persists after petal drop;

*Style*.—Straight; attitude mostly outwardly; about 7.0 mm long and 0.25 mm diameter; color nearest RHS 83A.

*Stigma*.—Globose; finely puberulent; about 0.3 mm in diameter; color RHS N92A.

*Ovary*.—Spherical to slightly elliptic; about 1.0 mm long and 0.8 mm in diameter; color nearest RHS 145B.

Sepals: Four, surface dull, ovate to narrowly ovate, acute apex, base fused forming campanulate calyx, puberulent margin; adaxial glabrous; abaxial nearly microscopically puberulent; about 3.0 mm long and 1.0 mm across;

Sepal color: Abaxial and adaxial between RHS 138A and RHS N138B;

Peduncle: Strong, erect, branched at nodes; terete; puberulent; about 50 cm long and 2.5 mm in diameter at the base; terminal flowering section of the main stem 12 to 18 cm long frequently split in two branches; attitude upwardly to slightly outwardly very late in flowering season; freely branching at distal nodes; about 7 to 8 nodes before flowers; average internode length about 3.0 cm;

Peduncle color: Between RHS 146A and RHS 137C;

Pedicel: Rigid, about 1.0 mm long and 0.3 mm wide, finely puberulent; attitude mostly outwardly;

Pedicel color: Between RHS N138B and RHS 138A;

Bract: One, subtending each flower, linear, acute apex, mostly entire, sessile, based fused to peduncle, proximal bracts about 6.5 cm long and 1.0 mm wide;

Bract color: Adaxial between RHS 137A and RHS 139A, and abaxial between RHS 137C and RHS 138A;

Fruit: Ellipsoid, about 3.0 mm long and 2.5 mm across; color between RHS 166A and RHS 166B;

Propagation: The plant roots from cuttings in about 2 weeks and finishes to flowering in a 3.8 liter container in 8 to 10 weeks following a vernalization period of about 8 weeks;

Hardiness, pest and disease resistance: The plant grows best with plenty of moisture and adequate drainage, but is able to tolerate some drought when mature. Hardiness at least from USDA zone 4 through 9. Disease and pest resistance beyond what is typical of that of other spike speedwell has not been observed.

It is claimed:

1. A new and distinct cultivar of ornamental spike speedwell plant, *Veronica* 'Blue Skywalker', as herein described and illustrated.

* * * * *